United States Patent [19]

Sweeney, Jr.

[11] Patent Number: 5,527,444
[45] Date of Patent: Jun. 18, 1996

[54] PROBE HAVING COAXIAL DESIGN FOR USE WITH DISSOLVED OXYGEN METER

[76] Inventor: John W. Sweeney, Jr., 100 Ogden St., New Haven, Conn. 06511

[21] Appl. No.: 229,567

[22] Filed: Apr. 19, 1994

[51] Int. Cl.⁶ .................................................. G01N 27/404
[52] U.S. Cl. ........................ 204/415; 204/412; 205/783
[58] Field of Search .............................. 204/153.18, 415, 204/412

[56] References Cited

U.S. PATENT DOCUMENTS

| | | |
|---|---|---|
| 2,901,327 | 8/1959 | Thayer . |
| 2,987,912 | 6/1961 | Jacobson . |
| 2,995,922 | 8/1961 | Firth . |
| 3,060,723 | 10/1962 | Kapff . |
| 3,068,684 | 12/1962 | Axt . |
| 3,113,092 | 12/1963 | Dowson ................................. 205/782 |
| 3,150,516 | 9/1964 | Linnenbom . |
| 3,198,000 | 8/1965 | Schlageter . |
| 3,218,242 | 11/1965 | Capuano ................................ 205/782 |
| 3,313,720 | 4/1967 | Robinson ................................ 205/782 |
| 3,319,159 | 5/1967 | Robinson . |
| 3,322,662 | 5/1967 | MacKereth ............................ 204/415 |
| 3,438,241 | 4/1969 | McKinley . |
| 3,510,406 | 5/1970 | Stack, Jr. .............................. 205/782 |
| 3,526,577 | 9/1970 | Molloy ................................... 204/415 |
| 3,764,504 | 10/1973 | Arff ....................................... 204/415 |
| 3,849,070 | 11/1974 | Garza . |
| 3,871,228 | 3/1975 | Weiss . |
| 3,962,046 | 6/1976 | Morrison ................................. 73/19 |
| 3,964,864 | 6/1976 | Dahms . |
| 3,988,233 | 10/1976 | Garner et al. ......................... 204/415 |
| 3,997,419 | 12/1976 | Scott ..................................... 204/415 |
| 4,058,447 | 11/1977 | Christiansen ......................... 204/415 |
| 4,172,770 | 10/1979 | Semersky et al. ................... 204/412 |
| 4,207,161 | 6/1980 | Pegnim ................................. 204/415 |
| 4,208,902 | 6/1980 | Kim . |
| 4,244,713 | 1/1981 | Goodwin . |
| 4,259,165 | 3/1981 | Miyake ................................. 204/415 |
| 4,461,165 | 7/1984 | Kesson . |
| 4,516,580 | 5/1985 | Polanyi . |
| 4,563,892 | 1/1986 | D'Aoust . |
| 4,598,576 | 7/1986 | Goldsmith . |
| 4,662,210 | 5/1987 | D'Aoust . |

*Primary Examiner*—T. Tung
*Attorney, Agent, or Firm*—St. Onge Steward Johnston & Reens

[57] ABSTRACT

A probe is disclosed for use with a dissolved gas meter, which is capable of measuring the concentration of dissolved gas in a fluid by measuring the permeation of gas through a membrane into an electrolyte solution. The probe includes an inner member, preferably tubular, disposed inside an outer member, preferably tubular, each tubular member having an open top end. Preferably, the inner tubular member and the outer tubular member are coaxially located such that an annular space is formed between the inner and outer tubular member. The probe further includes a plurality of electrodes operably connected inside the probe to the meter. A counter electrode extends into the central chamber of the inner tubular member, along the central axis. A working electrode is wrapped around the outer tubular member. A reference electrode is wrapped around the inner tubular member. A membrane, preferably made of silicone elastomer material, covers at least a portion of the outer tubular member and encloses the working electrode so as to form a pocket around a portion of the working electrode. Electrolyte solution is injected into the top of the inner tubular member and flows from a central chamber in the inner tubular member to the outside of the outer tubular member and around the working electrode through a series of holes, which create passages for the flow of the solution. As such, the electrodes are in at least in partial fluid communication with the electrolyte solution.

17 Claims, 4 Drawing Sheets

5,527,444

PROBE HAVING COAXIAL DESIGN FOR USE WITH DISSOLVED OXYGEN METER

FIELD OF THE INVENTION

The present invention relates to probes for use with meters for measuring a dissolved gas in an electrolytic solution, and more particularly, to dissolved oxygen meters that measure the amount of dissolved oxygen in a fluid, such as water.

BACKGROUND OF THE INVENTION

Dissolved oxygen meters and probes used to determine an amount of dissolved oxygen in a fluid are known. As is known in the art, a thin gas-permeable membrane isolates electrodes in the probe from their environment but allows oxygen and other gases to permeate through the membrane. When a voltage is applied across two of the electrodes, oxygen that is passed through the membrane reacts causing a current to flow. Measurement of this current can be interpreted by a microprocessor to measure the amount of dissolved oxygen. This amount is then displayed on a liquid-crystal display on the meter.

Probes that are generally able to measure changes in oxygen are known and commercially available. However, they are sometimes unable to calculate relatively small changes in the amount of dissolved oxygen. As such, these commercially available probes are less accurate than desirable.

This inability to accurately detect small changes in the amount of dissolved oxygen is largely due to at least two undesirable design arrangements. First, the surface area of one of the electrodes, sometimes called a working electrode, is generally small compared to the surface area of the membrane. Second, these probes typically have large volumes of electrolyte between the membrane and the working electrode.

These two design faults lead to an additional problem. Because large volumes of oxygen can pass through the membrane, it takes a fairly long time for this large volume of oxygen to be "consumed" and the probe reset to "zero". As such, much time is wasted during calibrations while the probe consumes this oxygen to reset itself; indeed, for this reason, calibration of true zero is typically not done.

Further, commercially available electrodes are undesirable because they generally require the end user to calibrate, or otherwise perform some preliminary function, before usage begins. This sometimes results in errors caused by the end user.

SUMMARY OF THE INVENTION

Accordingly, it is an object of the present invention to provide a probe for use with a control meter which can rapidly determine an amount of dissolved gas in a fluid.

It is another object of the present invention to provide a probe for use with a dissolved oxygen meter which can detect relatively small changes in the amount of dissolved oxygen.

It is yet another object to provide a probe which can be quickly reset to zero.

It is still another object of the present invention to provide a probe for use with a control meter which has a working electrode which has a large surface when compared to the surface area of the membrane.

It is a further object of the present invention to provide a probe for use with a control meter which has a reduced reservoir of electrolyte between the working electrode and the membrane, and is so constructed that (1) all oxygen is "scrubbed" by the working electrode before it can enter the rest of the probe, and (2) no oxygen enters the probe when not in operation.

It is still a further object to provide a probe which can be sold to a user in a "ready-to-use" manner, thus reducing the possibility of user calibration errors.

To overcome the deficiencies of the prior art and to achieve the objects listed above, a probe is disclosed for measuring the concentration of dissolved gas in a fluid by measuring the permeation of gas through a membrane into an electrolyte solution. In particular, the probe has an inner member, preferably tubular, and an outer member, preferably tubular, each of which has a top end, and each of which has a central axis therein. In the preferred embodiment, at least a portion of the inner tubular member is coaxially located inside the outer tubular member and fits loosely within the outer member such that a space, preferably annular, is formed therebetween.

The inner and the outer tubular members each have at least one hole or slot, and preferably a plurality of holes or slots. These holes allow electrolyte solution, which is injected into a central chamber of the inner tubular member, to flow from the central chamber, through the inner member, to substantially fill the annular space between the inner and outer tubular members. Electrolyte solution also flows through at least one of the holes in the outer tubular member to submerge at least a portion of the surface area of the outer tubular member.

A plurality of electrodes, disposed inside the probe, are operably connected to the control meter. In the preferred embodiment, a plurality of electrodes are connected, including a reference electrode, a working electrode and a counter electrode. The counter electrode extends into the central chamber of the inner tubular member and preferably extends substantially along the central axis of the inner and outer tubular member. Preferably, at least a portion of the working electrode is wrapped around at least a portion of the outer tubular member. Most preferably, at least a portion of the reference electrode is wrapped around at least a portion of the inner tubular member. The reference electrode, the working electrode, and the counter electrode are at least in partial fluid communication with the electrolyte solution.

A membrane, preferably a silicone elastomer, covers at least a portion of the outer tubular member. The membrane encloses a portion of the working electrode, and preferably contacts the working electrode, where the working electrode has been wrapped around the outer tubular member. Most preferably, there is a very short distance, or no distance, between the working electrode and an inner surface of the membrane.

In the preferred embodiment, because of the coaxial design, the working electrode is wrapped around the outer tubular member at least once and preferably twice, although the working electrode may be wrapped around the outer member any number of times, thus maximizing the surface area of the electrode exposed adjacent to the membrane.

Preferably, the reference electrode is wrapped around the inner tubular member at least once and preferably twice, although the reference electrode may be wrapped around the inner member any number of times. Most preferably the inner tubular member further comprises at least one groove which is adapted in size and shape to receive the reference electrode and contain it after it has been wrapped about the inner tubular member.

The probe further comprises a plug for closing the top open end of the inner tubular member. Electrolyte solution is inserted and removed from the central chamber of the inner tubular member through a syringe injected through the plug.

In operation, the probe is dropped into a fluid, such as water. The electrodes sense the amount of dissolved gas that permeates the membrane and send this data back to the control. The control, which is commonly known in the art, has means for interpreting this data and means for displaying the interpreted data.

Advantageously, because of the coaxial design, the surface area of the working electrode is very large compared to the active surface area of the membrane, that is, the permeable portion of the membrane. Further, because the surface area of the membrane is small compared to the surface area of the electrode and because the membrane contacts the electrode, the oxygen that permeates the membrane is quickly and totally consumed. Since the oxygen is totally consumed, the probe is readily reset and available for another test.

The invention and its particular features and advantages will become more apparent from the following detailed description when considered with reference to the accompanying drawings.

DETAILED DESCRIPTION OF THE DRAWINGS

Figure 1:
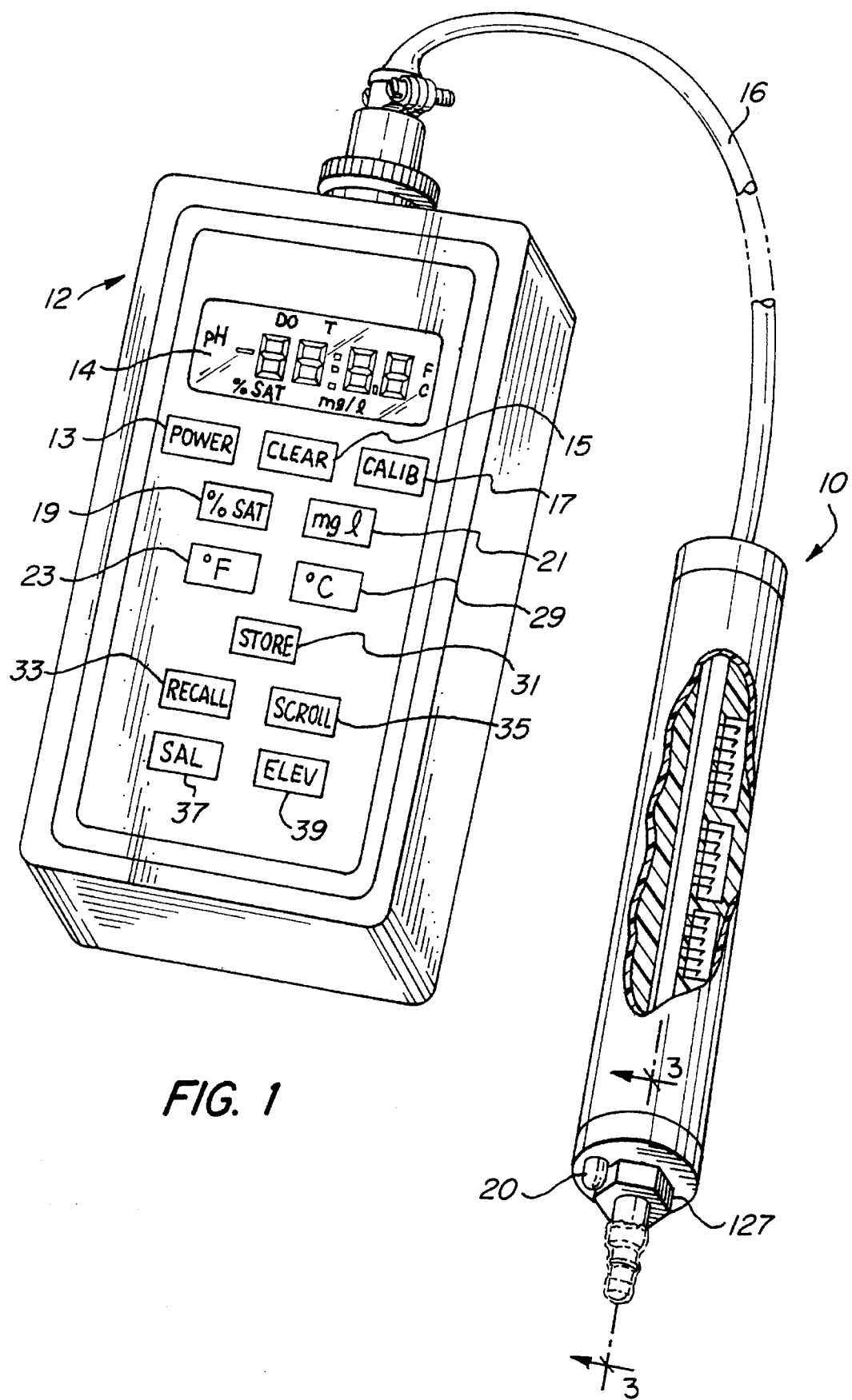
FIG. 1 is a perspective view of a dissolved oxygen meter and probe, constructed in accordance with the present invention, with a portion of a cable broken away.

Referring to the drawings in detail, a probe for use with a dissolved oxygen meter is shown and generally designated by the reference numeral 10. See FIGS. 1–5. It should be noted that for the sake of clarity not all the components and parts of probe 10 may be shown and/or marked in all the drawings. As used in this description, it should be understood that "tip" of probe 10 refers to the end of probe 10 having the smallest diameter, which is shown farthest to the right in FIGS. 3, 4, while "back" of probe 10 refers to that end of probe 10 farthest to the left in FIGS. 3, 4. As such, the "top" of probe 10 is generally the same as the "tip" of the probe and "bottom" of probe 10 is generally the same as "back" of probe 10.

Referring to FIG. 1, probe 10 sends data to control meter 12, sometimes called a control, or meter, which interprets the data through the use of a microprocessor operated circuit (not shown). Control meter 12 is generally known in the art. Control meter 12 displays readings on liquid crystal display 14. As such, meter 12 can read and display information, such as the concentration of dissolved oxygen, based on data gathered by and sent from probe 10. One suitable meter 12 was disclosed in U.S. patent application filed by Applicant on Feb. 18, 1994, entitled "Dissolved Oxygen Meter" and accorded Ser. No. 08/198,618, now abandoned. That application is hereby incorporated by reference.

Referring in particular to FIG. 1, control 12 comprises a printed circuit board with a series of computer chips and other components thereon connected to a power source such as a battery (not shown). As shown, a series of functions are available. "POWER" button 13 turns the device on and off. "CLEAR" button 15 functions to clear the memory of control 10. "CALIB" button 17 calibrates the probe 10.

There are two buttons for displaying the concentration of oxygen: "%SAT" button 19 shows the percentage of saturation of dissolved oxygen while "MgL" button 21 displays the concentration in milligrams per liter of dissolved oxygen.

If a temperature reading is desired, "° F." button 23 gives the temperature in "degrees Fahrenheit" while "° C." button 29 gives a reading in "degrees Celsius".

In accordance with one aspect of the invention, the control can store up to ten readings by pressing "STORE" button 31 before each reading. Thereafter, one can either recall a specific reading by pressing "RECALL" button 33 or can review a series of readings repeatedly depressing "SCROLL" button 35.

Because dissolved gas readings are sensitive to elevation and the salinity of the fluid being tested, "SAL" and "ELEV" buttons 37, 39 are provided. Before calibrating, one depresses "SAL" button 37 and enters a salinity reading by pushing "SCROLL" button 35 repeatedly. The elevation is entered by pressing "ELEV" button 39 and again depressing "SCROLL" button 35 repeatedly.

Probe 10 is connected to control meter 12 via cable 16, which also functions as a support line when probe 10 is dropped into a fluid, such as water, to be tested. See FIG. 1. Cable 16 includes electrical wiring (not shown) for operably connecting the circuitry within probe 10 to the circuitry within control meter 12.

Figure 2:
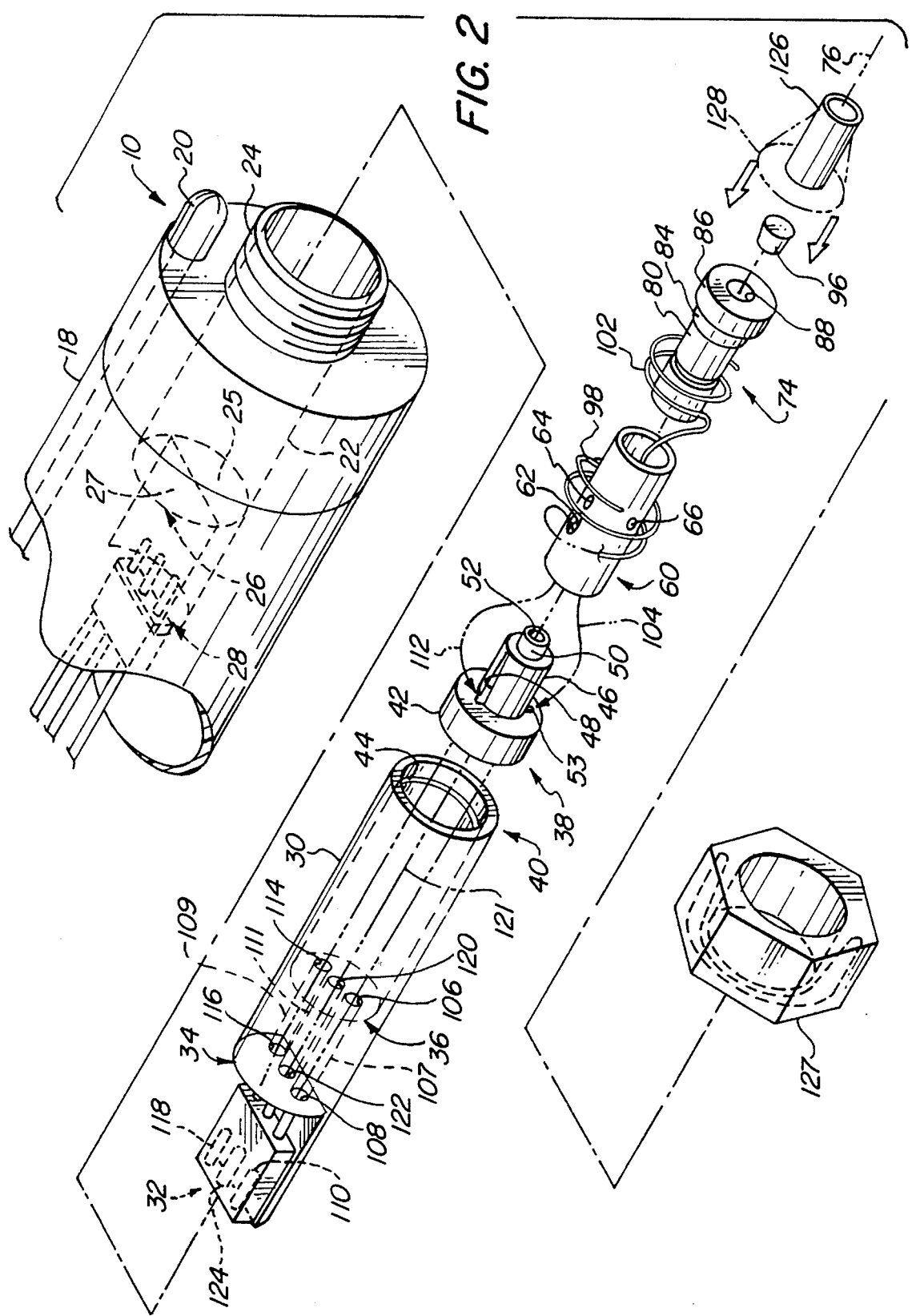
FIG. 2 is an exploded view of a front end of the probe, shown in FIG. 1, with portions broken away.
Figure 3:
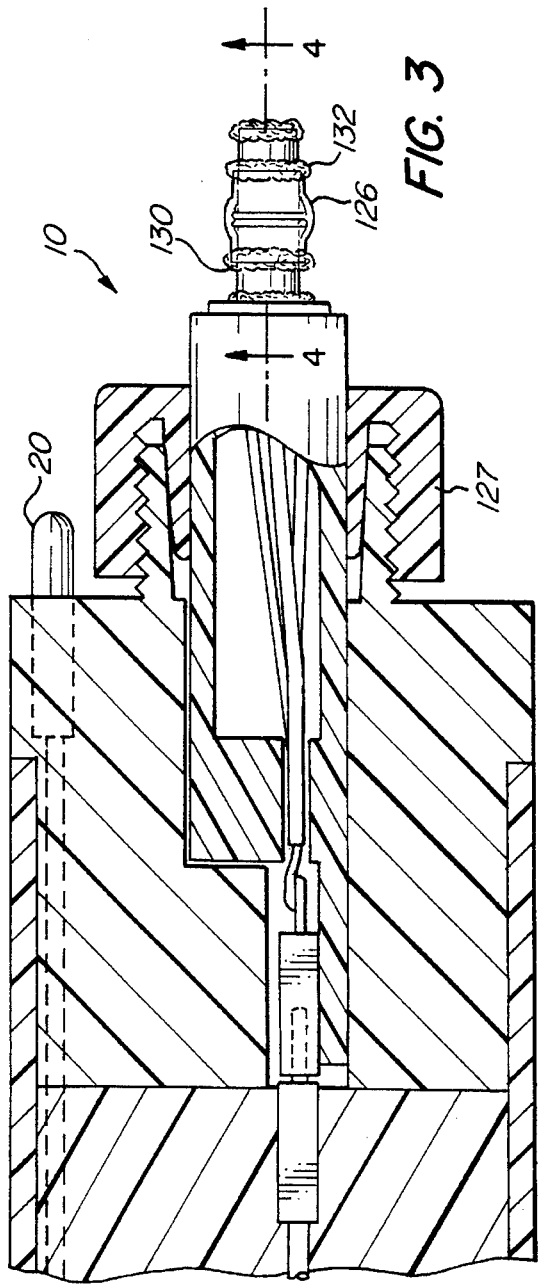
FIG. 3 is an enlarged cross sectional view of the front end of the probe, taken along line 3—3 of FIG. 1, with portions broken away.

As best shown in FIG. 2, probe 10 comprises primary housing 18. Primary housing 18 can be made of any suitable material, so long as the material is sufficiently impermeable to gas and water and is sufficiently electrically non-conductive. Most preferably, primary housing 18 is made of acrylic and is then cast, machined or, alternatively, molded to a desired shape. Advantageously, acrylic is clear, allowing a user to actually see if there are improper air bubbles or buildup of material extending from the counter electrode within probe 10. Gas impermeability is important for the material constituting the sensor module which, in FIG. 2, begins, in the exploded view, left to right, with guide piece 38 and includes neck 46, outer tubular member 60, and inner member 74.

Primary housing 18 further comprises thermistor 20 (FIGS. 1–3), which determines the temperature of the fluid into which probe 10 has been dropped, the results of which can be displayed on meter 12 display 14 (FIG. 1), as is known in the art. Any suitable thermistor 20 can be used such as that one made by Dale Electronics located in Norfolk, Nebr.

Referring to FIG. 2, primary housing 18 comprises secondary housing 22, which is preferably made of acrylic in the same manner as previously described for primary housing 18. At one end, secondary housing 22 has attached threaded connector 24, and at the other end has end piece 26 and male connectors 28. End piece 26 has a semicircular-shaped opening 25 and a semicircular-shaped closed portion 27.

Probe 10 further comprises tertiary housing 30, also preferably made of acrylic in the same manner as discussed above. Because acrylic is clear, a user can readily wee if there are improper air bubbles or an undesirable buildup of materials in probe 10.

Tertiary housing 30 is disposed within secondary housing 22. Tertiary housing 30 comprises female connectors 32, semicircular end portion 34 and a second spaced apart end portion 36. Semicircular end portion 34 of tertiary housing 30 cooperates with semicircular end piece 26 of secondary housing 22 such that semicircular end portion 34 of tertiary housing 30 can only pass through open portion 25 of end piece 26 when properly aligned. As such, this ensures that male connectors 28 and female connectors 32 are properly aligned and operably connected.

It should be understood that end portions 26, 34 can take on any size and shape, so long as end portions 26, 34 properly align male and female connectors 28, 32, respectively. That is, end portions 26, 34 need not be semicircular to be operative.

Guide piece 38, preferably made of acrylic in the manner discussed above, fits in end 40 of tertiary housing 30. Other gas-impermeable materials can be used. In particular, collar 42 of guide piece 38 fits against shoulder 44 of tertiary housing 30.

Guide piece 38 further comprises neck 46, attached to collar 42, which has slot 48. Preferably, slot 48 extends substantially the length of neck 46 and is, most preferably, beveled or angled to facilitate the insertion of an electrode into slot 48 as discussed below. Head 50, having opening 52, is attached to neck 46.

Figure 4:
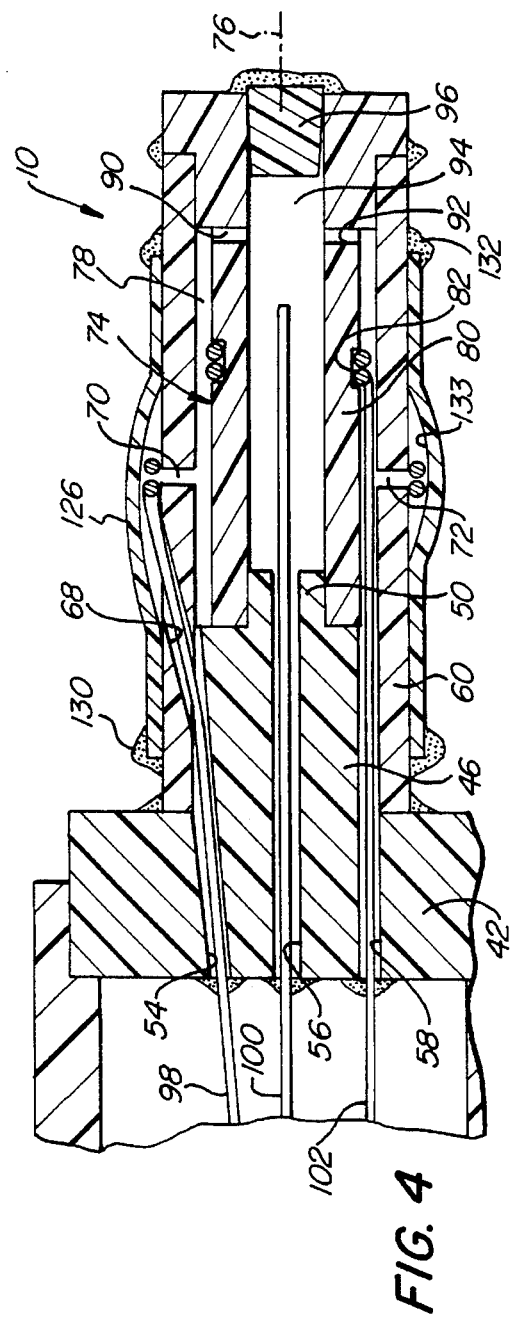
FIG. 4 is a cross sectional view of the probe, taken along line 4—4 of FIG. 3, with portions broken away.

As shown in comparing FIGS. 2, 4, beveled slot 48 leads to passage 54; opening 52 leads to passage 56, and hole 53 leads to passage 58. These passages 54, 56, 58 physically separate and allow for the passage of electrodes, as discussed below.

Outer member 60 extends over neck 46 and head 50 of guide piece 38 and abuts collar 42 of guide piece 38, as shown in FIGS. 2, 4. Outer tubular member 60 can be made of any suitable material, but is most preferably made of acrylic in the same manner as discussed above. Outer member 60 is preferably tubular, but may take on any shape so long as member 60 has a central axis therein.

Outer tubular member 60 further comprises a plurality of holes such as 62, 64, 66. At least one hole, such as 62, is of sufficient diameter to allow the insertion and removal of an electrode through it. Preferably, hole 62 is beveled so as to facilitate the insertion and removal of an electrode. Holes 62, 64, 66 (FIG. 2) lead to passages 68, 70, 72 (FIG. 4). Holes, such as 64, 66, leading to passages 70, 72 (FIG. 4) allow for the flow of electrolyte solution around the outer surface of outer tubular member 60, and need not be beveled.

As shown in FIGS. 2, 4, inner member 74 is substantially hollow and extends substantially along central axis 76. Inner member 74 is preferably tubular, but may be of any shape so long as member 74 has central axis 76.

Head 80 of inner tubular member 74 fits loosely within outer tubular member 60 so that an annular space 78 (FIG. 4) is provided between inner and outer tubular members 74, 60 respectively. In the preferred embodiment, annular space 78, or the distance between inner tubular member 74 and outer tubular member 60 is approximately 0.001 to about 0.002 inches. Annular space 78 should be sufficiently large to allow for the flow of electrolyte, but not so large as to house excess electrolyte solution.

Head 80 of inner tubular member 74 further comprises at least one groove 82 (see FIG. 4), extending about the circumference of inner member 74, of sufficient size to receive and hold an inserted electrode, after the electrode has been wrapped around head 80 at least once.

Inner tubular member 74 further comprises neck 84 and collar 86. Collar 86 of inner tubular member 74 acts as a stop means, when inner tubular member 74 is inserted into outer tubular member 60. Inner tubular member 74 further comprises passages 90, 92, as shown in FIG. 4, to facilitate the flow of electrolyte solution. Collar 86 of inner tubular member 74 has hole 88 leading to central chamber 94. See FIGS. 2, 4.

Plug 96 fits within hole 88 to close the open end of member 74 and to prevent leakage of electrolyte solution, injected by a syringe (not shown) through plug 96 into central chamber 94 (FIG. 4). Plug 96 may be made of any suitable material, so long as it is gas impermeable and electrically non-conducting. One suitable material is rubber.

In accordance with the invention, a plurality of hollow tube segments 98, 100, 102 extend substantially the length of probe 10 and are designed and arranged so as not to make physical contact with each other. Tube segments 98, 100, 102 are preferably made of silver, most preferably pure silver, or platinum.

Tubular segments 98, 100, 102 function as electrodes. More particularly, tubular segment 100 functions as a counter electrode. Preferably, counter electrode is made from pure silver which has been treated with chlorine to provide a silver chloride coating. Tubular member 102 functions as a reference electrode and is most preferably made of silver. Tubular segment 98 functions as a working electrode. Most preferably, working electrode 98 is made from platinum.

At least a portion of reference electrode 102 is wrapped at least once, and preferably twice, around the outer surface of head 80 of inner tubular member 74, although reference electrode 102 may be wrapped around inner member 74 any number of times. Most preferably, reference electrode 102 fits within groove 82 (FIG. 4) on outer surface of head 80 of inner tubular member 74. See FIG. 2. After winding reference electrode 102 around outer surface of head 80 of inner tubular member 74, reference electrode is then inserted through outer tubular member 60, around head 50 and neck 46 of guide piece 38 and through hole 53, along path indicated by dashed line 104 in FIG. 2. Reference electrode 102 extends through passage 58 (FIG. 4), into tertiary housing 30, through hole 106 of end piece 36 and hole 108 of end piece 34, connected by passage 107. Reference electrode 102 is then attached to a first portion 110 of female connector 32.

At least a portion of working electrode 98 is wrapped around outer surface of outer tubular member 60, at least once and preferably twice, although working electrode 98 may be wrapped as many times as desired. Working electrode 98 is then passed through hole 62, and is extended around head 50 of guide piece 38 and through beveled slot 48 of neck 46, along the path indicated by dashed line 112. See FIG. 2. Working electrode 98 then passes through hole 114 of end portion 36, through hole 116 of end portion 34, connected by passage 109, and is operably connected to a second portion 118 of female connector 32.

Referring to FIGS. 2, 4, counter electrode 100, which is positioned inside central chamber 94 of inner tubular member 74, and preferably along central axis 76, passes along dashed line 121, through hole 120 of end portion 36 and hole 122 of end portion 34, connected by passage 111, and is operably connected with third portion 124 of female connector 32.

After working electrode 98, reference electrode 102, and counter electrode 100 have been attached to respective portions of female connector 32, electrodes 98, 102 are pulled tight so as to be tight. See FIG. 4. That is, FIG. 2 shows electrodes 98, 102 loosely positioned (i.e., prior to being pulled tight), while FIG. 4 shows the electrodes positioned for use.

Flexible gas-permeable membrane 126 is positioned around at least a portion of the probe so as to form a pocket between the probe and the membrane. More particularly, membrane 126 is at least partially filled with electrolyte solution and covers at least a portion of working electrode 98, and preferably contacts working electrode at a plurality of points, after working electrode has been pulled tight. See FIGS. 2, 3, 4. Any suitable membrane may be used, such as a polymeric material that is permeable to the dissolved gas being measured. One suitable membrane is SILASTIC silicone elastomer, manufactured by Dow Corning. Another suitable material includes TEFLON tubing, made by Interplast of 1 Connecticut Drive, Burlington, N.J.

Membrane 126 may be of any suitable thickness, depending upon which type of material is used and the permeability of the material. When SILASTIC tubing is used, the membrane is preferably about 0.003 to about 0.006 inches thick after being stretched over probe. Prior to stretching, the thickness preferably ranges from about 0.004 to about 0.015 inches.

Membrane 126 is applied to outer tubular member 60 by pulling membrane 126 to substantially the size and shape shown by dashed line 128 by expanding membrane 126 in the direction of the arrows shown in FIG. 2.

Compression nut 127 is threaded onto threaded connector 24 to further make probe water and air-tight. See FIGS. 1–3.

To further make the interior of probe 10 water- and air-tight, sealant 130, 132 (FIGS. 3, 4) is applied to all areas where water or air may leak in. Sealant 130, 132 is preferably epoxy, or other suitable material, that hardens to provide a water and air tight seal. Other suitable sealants include silicone (RTV) or tetrachloroethylene ("GOOP").

Figure 5:
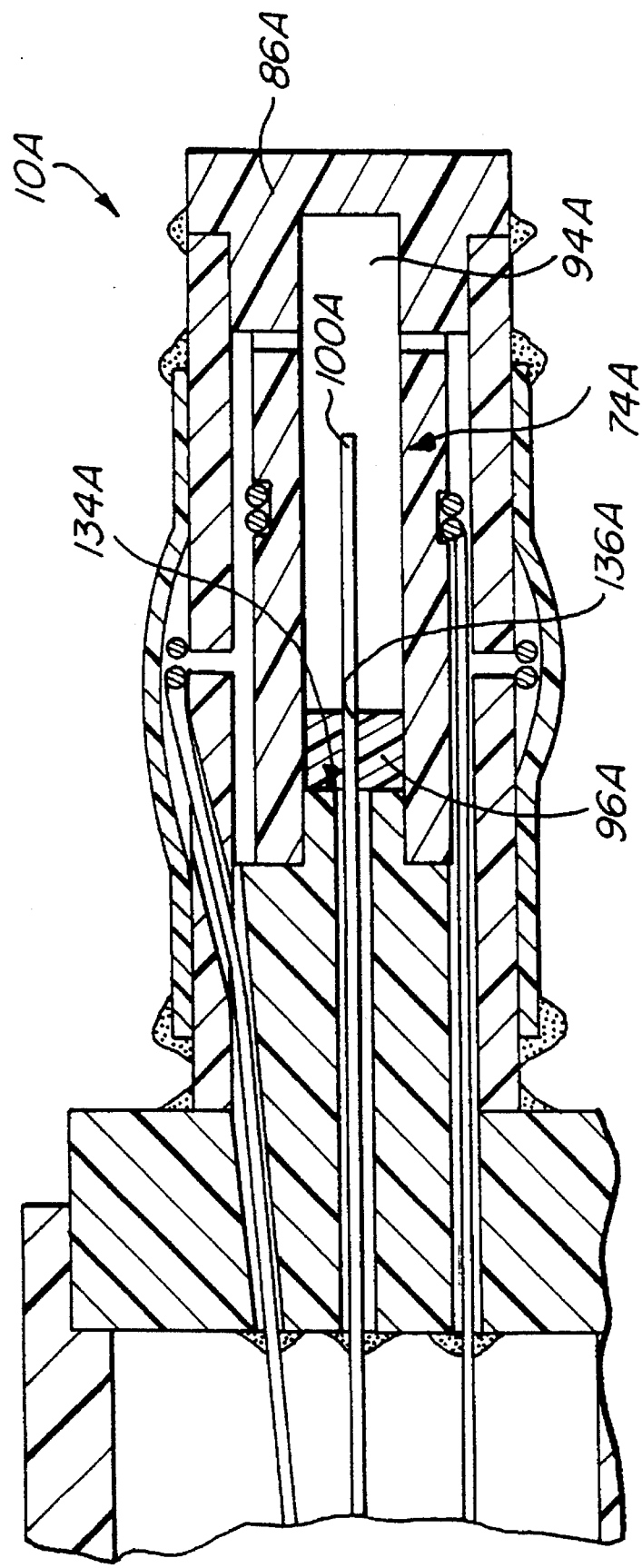
FIG. 5 is a cross-sectional view of an alternate embodiment of a probe, similar to FIG. 4, constructed in accordance with the present invention, and shows the altered location of the plug and an inner tubular member sealed at one end.

In another preferred embodiment, shown in FIG. 5, probe 10A comprises inner tubular member 74A having sealed, closed-ended collar 86A. Plug 96A abuts end 134A of central chamber 94A, and has hole 136A to allow for the passage of reference electrode 100A. Electrolyte solution is injected through plug 96A, but when comparing FIG. 5 to FIG. 4, in the alternate embodiment the injection occurs from the back end of probe 10A, rather than from the front end, or tip, of probe 10A. It should be understood that all other components of probe 10A are the same as previously described for probe 10, including the relationship of the working electrode to the membrane.

A probe constructed in accordance with the present invention provides a particularly fast response time. Because the volume of electrolyte between working electrode 98 and membrane 126 is small, and the surface area of the working electrode is large compared to the surface area 133 (FIG. 4) of membrane 126, the oxygen that permeates membrane 126 is consumed rapidly and in no more than a few seconds, and preferably less than one second.

In the preferred embodiment, the active surface area of working electrode 98 adjacent to membrane 126 is about 0.0133 inches squared to about 0.0311 inches squared. The relevant surface area 133 (FIG. 4) of membrane 126 is about 0.0258 inches squared to about 0.0320 inches squared. As such, the preferred ratio of surface area of the working electrode 98 to the membrane 126 is about 0.516 inches squared to about 0.972 inches squared.

Advantageously, a probe constructed in accordance with the present invention can be manufactured and calibrated at the factory. As such, the probe 10 requires no filling of electrolyte or affixing of membrane by the end user prior to testing. This reduces the possibility of errors committed by the end user.

Thus an oxygen meter in accordance with the present invention provides for a cheap and inexpensive probe that can be disposed of when use is completed. Alternatively, the probe can be easily recycled by injecting replacement electrolyte solution into the central chamber 94 or returning to the factory for refurbishment.

It should be understood that members 60, 74 need not be tubular to provide the desired co-axial design. That is, members 60, 74 could be any shape, such as square, so long as one of the members fits inside the other, leaving a workable space therebetween, and so long as the members were concentric.

It should be understood that if outer member 60 and inner member 74 were not tubular, then space 78 would not be annular, as previously described. As such, member 74 must be of sufficient size and shape to fit inside member 60 and allow for electrolyte solution therebetween.

It should be understood by those skilled in the art that obvious modifications can be made without departing from the spirit of the invention. Accordingly, reference should be made primarily to the accompanying claims, rather than the foregoing specification, to determine the scope of the invention.

We claim:

1. A dissolved gas meter for measuring the concentration of dissolved gas in a fluid by measuring the permeation of gas through a membrane into an electrolyte solution, comprising:

a probe for insertion into a fluid, the probe having an inner tubular member positioned about a central axis, and an outer tubular member coaxially positioned about the central axis of the inner tubular member, at least a portion of the inner tubular member being coaxially located inside the outer tubular member such that an annular space is formed therebetween, the inner tubular member defining a central chamber therein, the inner and outer tubular members each having a plurality of holes, at least one hole providing fluid communication between the central chamber of the inner tubular member, the annular space between the inner and outer tubular members, and substantially around the outer tubular member, and electrolyte solution substantially filling the central chamber inside the inner tubular member and substantially filling the annular space between the inner and outer tubular members;

a plurality of electrodes inside the probe including:

a counter electrode extending substantially along the central axis of the inner tubular member and into the central chamber inside the inner tubular member;

a working electrode extending about the outer tubular member and through at least one of the holes in the outer tubular member;

a reference electrode extending about the inner tubular member and through at least a portion of the outer tubular member; and the reference electrode, the working electrode, and the counter electrode being at least in partial fluid communication with the electrolyte solution; and a permeable membrane covering at least a portion of the outer tubular member and at least a portion of the working electrode such that a dissolved gas permeates the membrane, enters into the probe and is detected by the electrodes.

2. The dissolved gas meter of claim 1, the inner tubular member further comprising at least one groove extending about the circumference of the inner tubular member, the groove being adapted in size and shape such that the reference electrode, when inserted into the groove, fits therein.

3. The dissolved gas meter of claim 1, wherein at least one of the holes in the outer tubular member is beveled so as to facilitate insertion of the working electrode into the hole.

4. The dissolved gas meter of claim 1, the inner tubular member comprising a hole at a top end thereof, the probe further comprising a plug for closing the top open end of the inner tubular member.

5. The dissolved gas meter of claim 1, further comprising a control, operably connected to the probe, having means for interpreting data sensed by the electrodes in the probe and means for displaying the interpreted data.

6. A meter for measuring the concentration of dissolved gas in a fluid by measuring the permeation of gas through a membrane into an electrolyte solution, comprising:

a probe for insertion into a fluid, the probe having an inner tubular member positioned about a central axis, and an outer tubular member coaxially positioned about the central axis of the inner tubular member, each having a top end and a bottom end, at least a portion of the inner tubular member being coaxially located inside the outer tubular member such that an annular space is formed therebetween, the inner tubular member defining a central chamber therein, the inner and outer tubular members each having a plurality of holes, at least one hole providing fluid communication between the central chamber of the inner tubular member, the annular space between the inner and outer tubular members, and substantially around the outer tubular member, the inner tubular member being closed at the top end, the electrolyte solution substantially filling the central chamber inside the inner tubular member and substantially filling the annular space between the inner and outer tubular members;

a plurality of electrodes inside the probe including:
a counter electrode extending substantially along the central axis of the inner tubular member and into the central chamber inside the inner tubular member;
a working electrode extending about the outer tubular member and extending through at least one of the holes in the outer tubular member;
a reference electrode extending about the inner tubular member and through at least a portion of the outer tubular member; and
the reference electrode, the working electrode, and the counter electrode being at least in partial fluid communication with the electrolyte solution;

a permeable membrane covering at least a portion of the outer tubular member and the working electrode, such that a dissolved gas permeates the membrane, enters into the probe and is detected by the electrodes; and a plug, inside the inner tubular member and at substantially the bottom end of the inner tubular member, having a hole for receiving the reference electrode.

7. The meter of claim 6, the inner tubular member further comprising at least one groove extending about the circumference of the inner tubular member, the groove being adapted in size and shape such that the reference electrode, when inserted into the groove, fits therein.

8. The meter of claim 6, wherein at least one of the holes in the outer tubular member is beveled so as to facilitate insertion of the working electrode into the hole.

9. The meter of claim 6, further comprising a control, operably connected to the probe, having means for interpreting data sensed by the electrodes in the probe and means for displaying the interpreted data.

10. A dissolved gas meter for measuring the concentration of dissolved gas in a fluid by measuring the permeation of gas through a membrane into an electrolyte solution, comprising:

a probe for insertion into the fluid, the probe having an inner member positioned about a central axis and an outer member coaxially positioned about the central axis of the inner tubular member, at least a portion of the inner member being coaxially located inside the outer member such that a space is formed between the inner and outer members, the inner member defining a central chamber therein, the inner and outer members each having a plurality of holes, at least one hole providing fluid communication between the central chamber of the inner member, the space between the inner and outer members, and substantially around the outer member, the electrolyte solution substantially filling the central chamber inside the inner member and substantially filling the space between the inner and outer members;

a plurality of electrodes inside the probe including:
a counter electrode extending substantially along the central axis of the inner member and into the central chamber inside the inner member;
a working electrode extending about the outer member and through at least one of the holes in the outer member;
a reference electrode extending about the inner member and through at least a portion of the outer member; and
the reference electrode, the working electrode, and the counter electrode being at least in partial fluid communication with the electrolyte solution; and a permeable membrane, covering at least a portion of the outer member and at least a portion of the working electrode so as to form a pocket for enclosing the working electrode and exposing a portion of the working electrode to electrolyte solution, wherein a dissolved gas permeates the membrane, enters into the probe and is detected by the electrodes.

11. The dissolved gas meter of claim 10, wherein the outer member is tubular.

12. The dissolved gas meter of claim 11, wherein the inner member is tubular.

13. The dissolved gas meter of claim 10, the inner member further comprising a top, and the probe further comprising a plug for closing the top of the inner member.

14. The dissolved gas meter of claim 13, the inner member being sealed at the top, and the probe further comprising a plug, opposite the sealed end of the inner member, the plug having means for receiving the reference electrode.

15. The dissolved gas meter of claim 10, wherein the membrane is in direct contact with the working electrode.

16. The dissolved gas meter of claim 10, wherein at least one of the holes in the outer member is beveled so as to facilitate insertion of the working electrode into the hole.

17. The dissolved gas meter of claim 10, the inner member further comprising at least one groove extending about the inner member, the groove being adapted in size and shape such that the reference electrode, when inserted into the groove, fits therein.

* * * * *